US00PP21287P2

(12) United States Plant Patent
Harp

(10) Patent No.: US PP21,287 P2
(45) Date of Patent: Sep. 14, 2010

(54) ***ILLICIUM* PLANT NAMED 'PINK FROST'**

(50) Latin Name: *Illicium floridanum*
Varietal Denomination: Pink Frost

(75) Inventor: Mickey Harp, Fayetteville, GA (US)

(73) Assignee: Plant Introductions, Inc., Watkinsville, GA (US)

( * ) Notice: Subject to any disclaimer, the term of this patent is extended or adjusted under 35 U.S.C. 154(b) by 0 days.

(21) Appl. No.: 12/456,284

(22) Filed: Jun. 15, 2009

(51) Int. Cl.
*A01H 5/00* (2006.01)

(52) U.S. Cl. ..... Plt./226

(58) Field of Classification Search ..... Plt./226
See application file for complete search history.

(56) References Cited

OTHER PUBLICATIONS

Trade brochure distributed at Southern Nursery Association Tradeshow, Atlanta, Georgia, Feb. 12-13, 2009.

*Primary Examiner*—Annette H Para
(74) *Attorney, Agent, or Firm*—Greenlee Winner and Sullivan PC

(57) ABSTRACT

A new and distinct cultivar of *Illicium* plant named 'Pink Frost', characterized by its compact, rounded growth habit, medium green foliage with cream-white marginal variegation, pink-red petioles, red flowers, and pink to red foliage in winter.

5 Drawing Sheets

Genus and species of plant claimed: *Illicium floridanum.*

Variety denomination: 'Pink Frost'.

BACKGROUND OF THE INVENTION

The present invention relates to a new and distinct cultivar of *Illicium* plant, botanically known as *Illicium floridanum,* and hereinafter referred to by the cultivar name 'Pink Frost'.

The new *Illicium* plant originated as a branch mutation on a container-grown *Illicium floridanum* in a cultivated environment at Fayetteville, Ga. in 2003.

Asexual reproduction of the new cultivar by stem cuttings at Watkinsville, Ga. since 2005 has shown that all the unique features of this new *Illicium,* as herein described, are stable and reproduced true-to-type through successive generations of such asexual propagation.

SUMMARY OF THE INVENTION

Plants of the new cultivar 'Pink Frost' have not been observed under all possible environmental conditions. The phenotype may vary somewhat with changes in light, temperature, soil and rainfall without, however, any variance in genotype.

The following traits have been repeatedly observed and are determined to be unique characteristics of 'Pink Frost'. These characteristics in combination distinguish 'Pink Frost' as a new and distinct cultivar: 1. Compact, rounded growth habit; 2. Medium green foliage with cream-white marginal variegation; 3. Pink-red petioles; 4. Red flowers; and 5. Pink to red foliage in winter.

Plants of the new *Illicium* 'Pink Frost' differ from plants of the parent, *Illicium floridanum,* primarily in foliage color, as plants of 'Pink Frost' have medium green foliage with cream-white marginal variegation, whereas plants of the parent have medium green foliage with no variegation.

Plants of the new *Illicium* can be compared to plants of *Illicium floridanum* forma variegatum Gaddy (U.S. Plant Pat. No. 16,269). However, in side-by-side comparisons conducted at Watkinsville, Ga., plants of the new *Illicium* differed from plants of *Illicium floridanum* forma variegatum Gaddy in the following characteristics: 1. Plants of the new *Illicium* had regular, elliptical-shaped, medium green foliage with uniform cream-white marginal variegation, whereas plants of *Illicium floridanum* forma variegatum Gaddy commonly had distorted, asymmetrical foliage with curved apices that was gray-green in color with irregular white to yellow marginal variegation; 2. Plants of the new *Illicium* had red flowers, whereas plants of *Illicium floridanum* forma variegatum Gaddy had white to pale pink flowers; and 3. Plants of the new *Illicium* rooted faster, produced saleable plants quicker, grew better, and were more cold hardy than plants of *Illicium floridanum* forma variegatum Gaddy.

BRIEF DESCRIPTION OF THE DRAWINGS

The accompanying color photographs illustrate the flower and foliage characteristics and the overall habit of the new *Illicium,* showing the colors as true as it is reasonably possible to obtain in color reproductions of this type. Colors in the photographs may differ slightly from the color values cited in the detailed botanical description which accurately describe the colors of the new *Illicium.*

DETAILED DESCRIPTION

Figure 1:
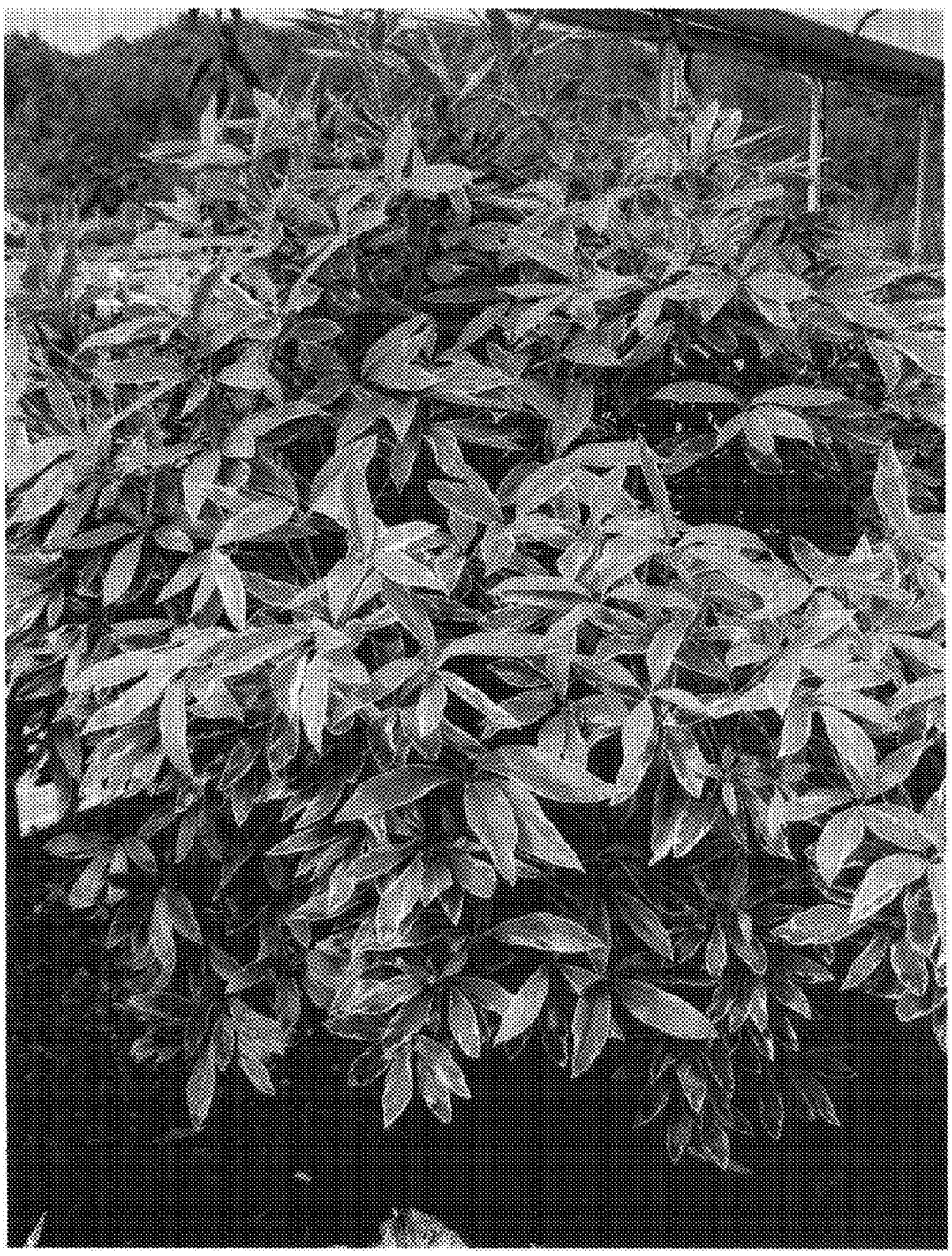
FIG. 1 illustrates the overall appearance and growth habit of a mature plant of 'Pink Frost'.
Figure 2:
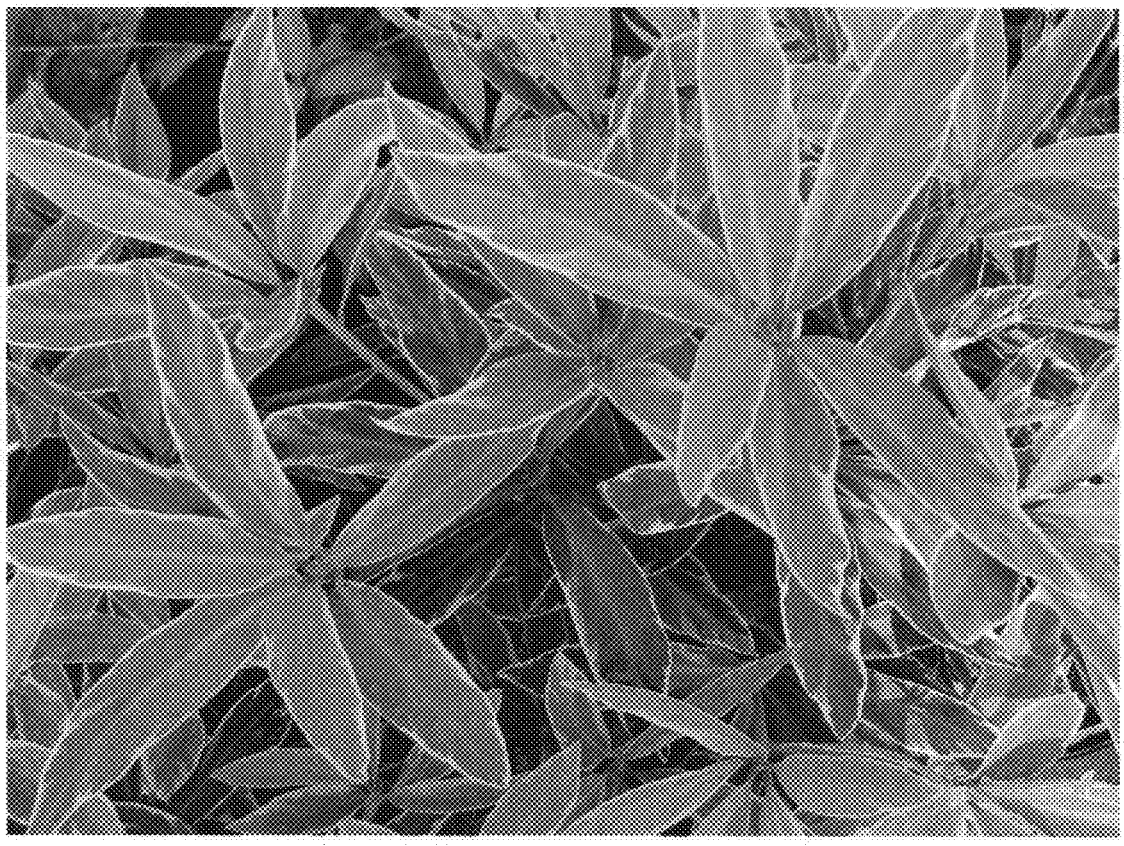
FIG. 2 illustrates a close-up view of the summer foliage of 'Pink Frost'.
Figure 3:
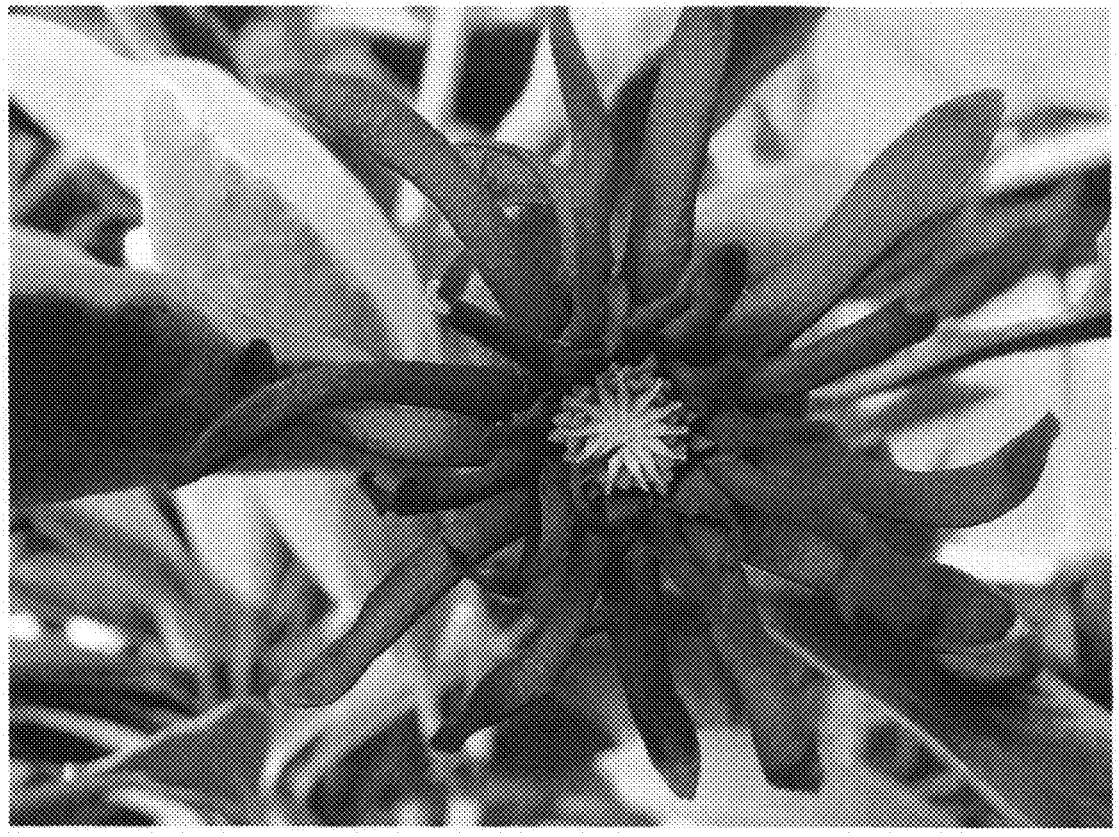
FIG. 3 illustrates a close-up view of the flower of 'Pink Frost'.
Figure 4:
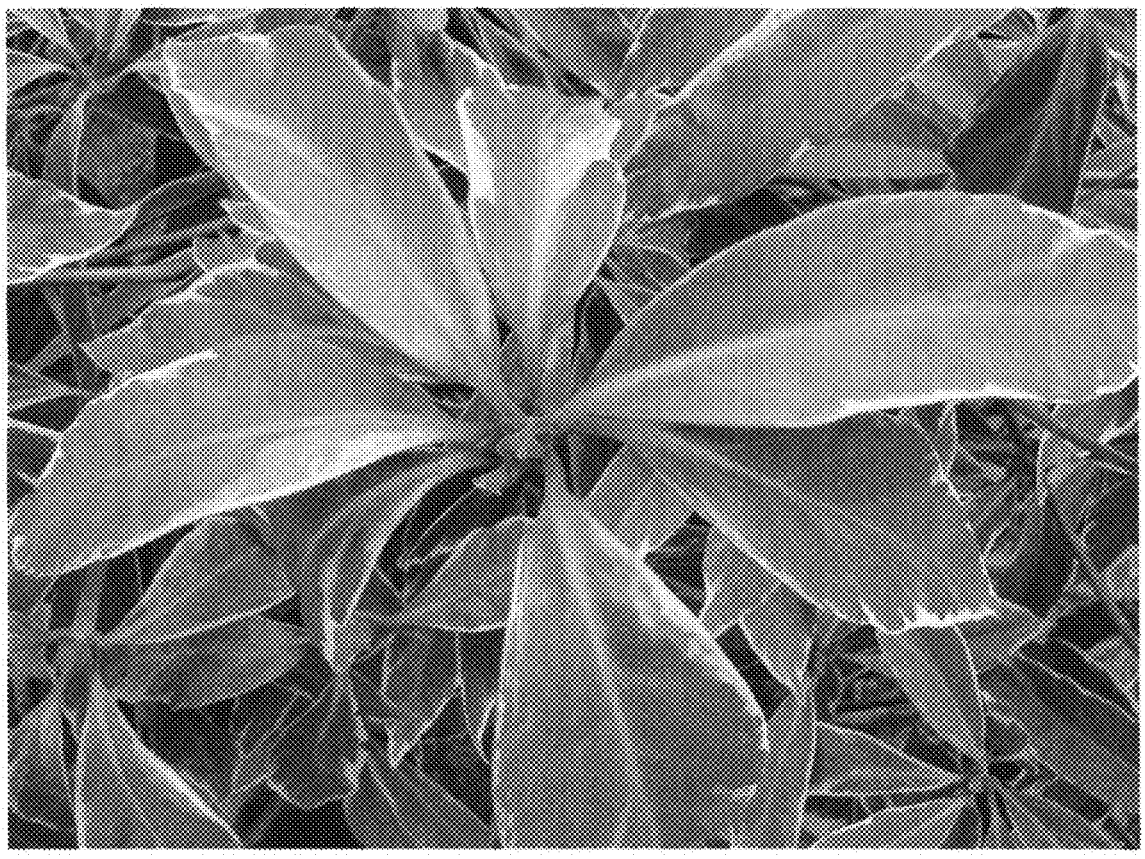
FIG. 4 illustrates the winter foliage of 'Pink Frost'.
Figure 5:
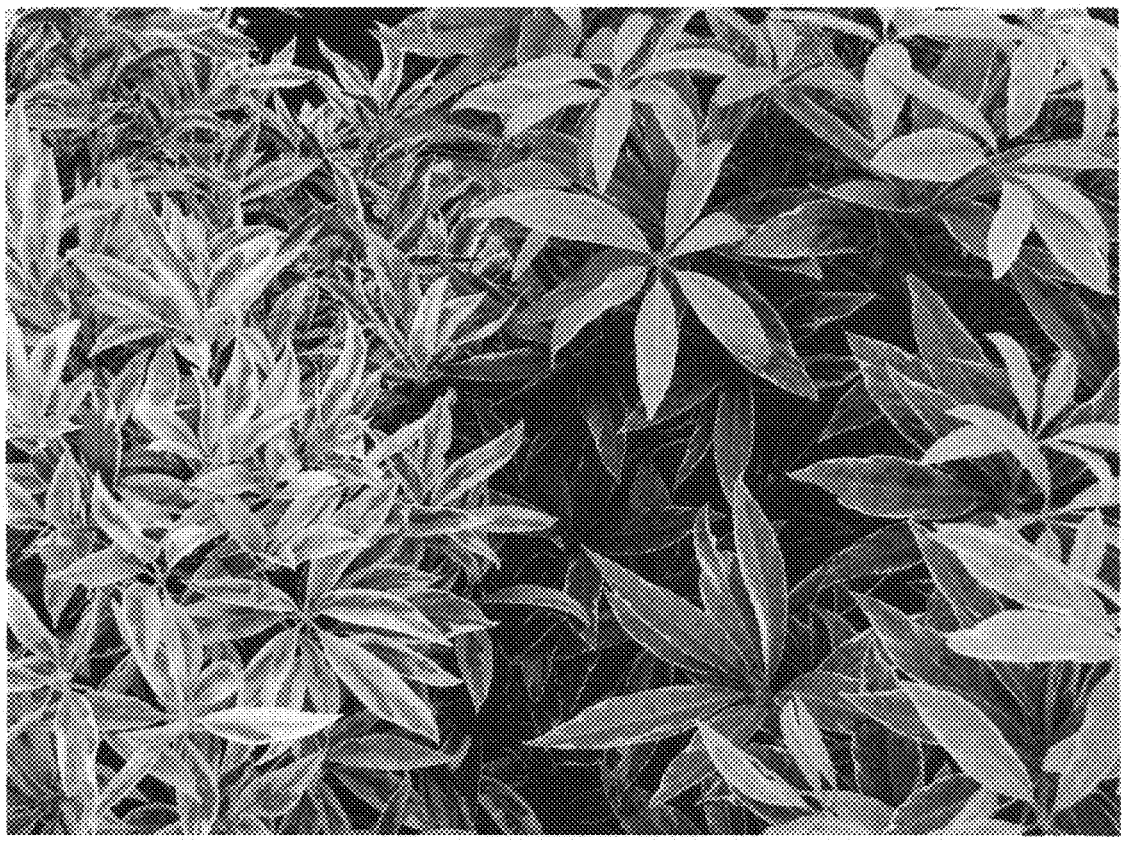
FIG. 5 illustrates a comparison of 'Pink Frost' (right) to *Illicium floridanum* forma variegatum Gaddy (left) during summer.

In the following description, color references are made to The Royal Horticultural Society Colour Chart, 2001 Edition, except where general terms of ordinary dictionary significance are used. Plants used for the description were grown under outdoor conditions at Watkinsville, Ga. Plants were about 4 years old when the description was recorded. Colors are described using The Royal Horticultural Society Colour Chart (R.H.S.).

*Botanical classification.*—*Illicium floridanum,* cultivar 'Pink Frost'. Parentage: *Illicium floridanum.* Propagation: terminal cuttings. Time to initiate roots in summer: about 6 weeks at 32° C.

Plant description: Broadleaf evergreen flowering shrub; multi-stemmed; compact, rounded growth habit. Freely branching; removal of the terminal bud enhances lateral branch development.

*Root description.*—Coarse, well-branched.

*Plant size at maturity.*—About 2 to 3 m high and wide. Lateral branches range in length from about 15 to 30 cm, with a diameter of about 5 mm. Shape: round.

*Strength.*—Easily broken.

*Internode length.*—About 5.7 cm.

*Texture.*—Glabrous, no pubescence.

*Stem color* (*young*).—Close to 145A. Color (mature/woody): close to 176B.

Vegetative bud description:

*Arrangement.*—Alternate to pseudo-whorled.

*Shape.*—Ovoid.

*Size.*—About 2 mm in length and about 1 mm in width.

*Color.*—Close to 145A, maturing close to 176B.

Foliage description:

*Arrangement.*—Alternate to pseudo-whorled, simple. Length: about 10 cm. Width: about 4 cm. Shape: elliptical. Apex: acute. Base: cuneate. Margin: entire.

*Texture.*—Thick, leathery.

*Venation pattern.*—Pinnate. Venation color: close to 144A.

*Fragrance.*—Strong, anise-like.

*Color in developing foliage* (*upper and lower surfaces*).—Close to N144C in the center with 150C margins. Color in mature foliage (upper surface): close to 137A in the center with 154D margins. Color in mature foliage (lower surface): close to 137C in the center with 154D margins. Color of winter foliage (upper and lower surfaces): same as mature foliage, except that it is overlaid with 48A.

*Petiole length.*—About 1 cm. Petiole diameter: about 2 mm. Petiole texture: glabrous. Petiole color: close to 176B.

Flower description:

*Flower type and habit.*—Flowers borne singly. Natural flowering season: late winter to early spring, approximately mid march in Watkinsville, Ga.

*Fragrance.*—Malodorous.

*Flower buds.*—About 9 mm in length and 7 mm in width. Shape: oblong. Color: close to 182A.

*Flower size.*—About 4 cm in diameter. Shape: round.

*Pedicels.*—About 5.5 cm in length. Color: close to 144B.

Petals:

*Petal size.*—Approximately 20 petals per flower, about 1.7 cm in length and about 3 mm in width.

*Petal shape.*—Strap-shaped. Margin: entire. Texture: smooth.

*Petal color.*—close to 187C.

Stamens:

*Quantity/arrangement.*—Many, about 35 per flower. Size: about 2 mm in length and about 1 mm in width. Color: close to 187B.

Pistil:

*Position.*—Superior. Size: about 5 mm in length and about 6 mm in width. Color: close to 145C. Stigma: about 14 per flower. Style: about 2 mm in length.

Fruit: Fruit production has never been observed.

Disease/pest resistance: Plants of the new *Illicium* grown in the garden have not been noted to be susceptible to pathogens and pests common to *Illicium.*

Weather and temperature tolerance: Plants of the new *Illicium* have been observed to be cold hardy to about USDA Hardiness Zone 6.

I claim:

1. A new and distinct *Illicium* plant named 'Pink Frost', as illustrated and described herein.

* * * * *